US008551034B2

(12) United States Patent
Dougherty, Jr.

(10) Patent No.: US 8,551,034 B2
(45) Date of Patent: *Oct. 8, 2013

(54) LUBRICIOUS COMPOSITIONS AND ARTICLES MADE THEREFROM

(75) Inventor: Eugene P. Dougherty, Jr., Camden-Wyoming, DE (US)

(73) Assignee: Playtex Products, LLC, Shelton, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/281,992

(22) Filed: Oct. 26, 2011

(65) Prior Publication Data

US 2012/0041354 A1 Feb. 16, 2012

Related U.S. Application Data

(63) Continuation of application No. 11/888,966, filed on Aug. 3, 2007, now Pat. No. 8,070,710.

(60) Provisional application No. 60/835,579, filed on Aug. 4, 2006.

(51) Int. Cl.
*A61F 13/32* (2006.01)
*A61F 13/28* (2006.01)
*C08K 5/20* (2006.01)
*C08L 23/04* (2006.01)

(52) U.S. Cl.
USPC .......... 604/18; 604/15; 604/12; 604/13; 604/11; 524/232; 524/230

(58) Field of Classification Search
USPC .......... 524/230, 210, 394, 400, 585, 486, 524/586, 587, 232; 604/18, 15
See application file for complete search history.

(56) References Cited

U.S. PATENT DOCUMENTS

| | | | | |
|---|---|---|---|---|
| 3,562,291 A | * | 2/1971 | Lutzman et al. | 524/231 |
| 3,851,781 A | * | 12/1974 | Marco | 215/11.3 |
| 3,940,325 A | | 2/1976 | Hirao | |
| 4,276,881 A | * | 7/1981 | Lilaonitkul | 604/14 |
| 4,321,993 A | | 3/1982 | Hinzmann et al. | |
| 4,361,150 A | | 11/1982 | Voss | |
| 4,410,649 A | * | 10/1983 | Cieloszyk | 524/108 |
| 4,768,987 A | | 9/1988 | Usui et al. | |
| 4,973,302 A | | 11/1990 | Armour et al. | |
| 5,001,182 A | * | 3/1991 | Maruya et al. | 524/427 |
| 5,135,475 A | * | 8/1992 | Nakanishi et al. | 604/14 |
| 5,204,402 A | * | 4/1993 | Foster et al. | 524/450 |
| 5,206,273 A | | 4/1993 | Chen et al. | |
| 5,225,466 A | | 7/1993 | Akao | |
| 5,262,459 A | * | 11/1993 | Kotani et al. | 524/91 |
| 5,306,542 A | | 4/1994 | Bayer | |
| 5,331,019 A | * | 7/1994 | Payne et al. | 522/75 |
| 5,389,067 A | | 2/1995 | Rejai | |
| 5,461,093 A | * | 10/1995 | Yoo et al. | 524/47 |
| 5,569,177 A | * | 10/1996 | Fox et al. | 604/15 |
| D376,430 S | | 12/1996 | Humphrey et al. | |
| 5,601,530 A | | 2/1997 | Nielson et al. | |
| 5,613,657 A | * | 3/1997 | Olaiz | 248/102 |
| 5,674,239 A | | 10/1997 | Zadini | |
| 5,681,894 A | * | 10/1997 | Williams et al. | 525/89 |
| 5,827,214 A | | 10/1998 | Fox et al. | |
| 5,962,094 A | | 10/1999 | Osterkamp et al. | |
| 5,986,000 A | | 11/1999 | Williams et al. | |
| 6,016,929 A | * | 1/2000 | Williams | 215/11.1 |
| 6,051,164 A | * | 4/2000 | Samuels | 252/404 |
| 6,254,565 B1 | | 7/2001 | Williams et al. | |
| 6,437,031 B1 | | 8/2002 | Lensvelt et al. | |
| 6,660,358 B2 | * | 12/2003 | Kaufman et al. | 428/67 |
| 6,673,032 B2 | | 1/2004 | Buzot | |
| 6,706,942 B1 | | 3/2004 | Zhao et al. | |
| 6,756,434 B1 | * | 6/2004 | Williams et al. | 524/132 |
| 7,182,987 B2 | * | 2/2007 | Matthijs et al. | 428/36.9 |
| 7,385,004 B2 | | 6/2008 | Wood | |
| 7,420,010 B2 | * | 9/2008 | Sukhadia et al. | 524/394 |
| 8,221,374 B2 | * | 7/2012 | Hou et al. | 604/385.17 |
| 2004/0030287 A1 | | 2/2004 | Matthijs et al. | |
| 2004/0188888 A1 | | 9/2004 | Putnam et al. | |
| 2004/0199102 A1 | | 10/2004 | LeMay et al. | |
| 2004/0225269 A1 | | 11/2004 | Zhao et al. | |
| 2004/0236266 A1 | | 11/2004 | Hull, Jr. | |
| 2004/0242803 A1 | | 12/2004 | Ohme et al. | |
| 2004/0260001 A1 | | 12/2004 | Lin et al. | |
| 2005/0070645 A1 | | 3/2005 | Williams et al. | |
| 2005/0096617 A1 | | 5/2005 | Gorham et al. | |
| 2005/0148720 A1 | | 7/2005 | Li et al. | |
| 2007/0167902 A1 | | 7/2007 | Edgett et al. | |

FOREIGN PATENT DOCUMENTS

| | | |
|---|---|---|
| EP | 0 268 843 | 6/1988 |
| GB | 2 153 684 A * | 8/1985 |
| GB | 2 353 038 | 2/2001 |

(Continued)

OTHER PUBLICATIONS

JP 07-080958 A (Mar. 1995) abstract and translation in English.*
JP 11-049903 A (Feb. 1999) abstract and translation in English.*
International Preliminary Report on Patentibility from corresponding PCT Application No. PCT/US2007/17388 dated Oct. 7, 2009.
International Search Report for International Application No. PCT/US2007/17388 dated Aug. 18, 2008.
Written Opinion for International Application No. PCT/US2007/17388 dated Aug. 18, 2008.
Supplementary European Search Report dated Jan. 28, 2010 from corresponding European Application No. 07836495.7.
"Selecting Amide Slip Concentrates for Polyethylene Film Applications", http://web.archive.org/web/200304100600923/ http://www.colortech-inc.com/?page=amideslip dated Apr. 10, 2003 (5 pps.).
European Examination Report dated Oct. 13, 2010 from corresponding European Application No. 07836495.7.
Official Action dated Jul. 28, 2010 from corresponding Russian Application No. 2009104775 (with English translation).
Notice of Reasons for Rejection dated Aug. 29, 2011 from corresponding Japanese Application No. 2009-523793.
Official Action dated Jul. 11, 2012 from corresponding Colombian Application No. 09012652 (with English summary).
Office Action dated Aug. 8, 2012 from corresponding Japanese Application No. 2009-523793 (with English translation).

*Primary Examiner* — Rip A. Lee

(74) *Attorney, Agent, or Firm* — Ohlandt, Greeley, Ruggiero, & Perle, L.L.P.

(57) ABSTRACT

The present disclosure provides a lubricious polymeric composition that includes polymer and one or more lubricants. Articles formed from the lubricious polymeric composition possess enhanced softness, flexibility and lubricity. The present disclosure also provides a method for making an article formed from a lubricious polymeric composition having polymer and one or more lubricants.

5 Claims, No Drawings

(56) References Cited

FOREIGN PATENT DOCUMENTS

| | | |
|---|---|---|
| JP | 6 72422 | 3/1994 |
| JP | 07-080958 A * | 3/1995 |
| JP | 11-049903 A * | 2/1999 |
| TW | 256846 | 9/1995 |
| WO | 0112715 | 2/2001 |
| WO | WO 01/32938 A1 * | 5/2001 |
| WO | 2004101683 | 11/2004 |
| WO | 2006124369 | 11/2006 |

\* cited by examiner

LUBRICIOUS COMPOSITIONS AND ARTICLES MADE THEREFROM

CROSS-REFERENCE TO RELATED APPLICATIONS

The present application a continuation of U.S. patent application Ser. No. 11/888,966, filed on Aug. 3, 2007, now U.S. Pat. No. 8,070,710, which in turn claims priority to U.S. Provisional Application No. 60/835,579, filed on Aug. 4, 2006.

BACKGROUND OF THE INVENTION

1. Field of the Invention

The present disclosure is directed to lubricious compositions.

The present disclosure is directed to lubricious compositions. More particularly, the present disclosure is directed to molded articles, such as tampon applicators, made from lubricious compositions.

2. Description of Related Art

Consumers are interested in tampon applicators that are soft, comfortable to insert, and easy to eject the pledgets from, under a variety of different environmental conditions. Additionally, some consumers experience vaginal dryness and especially desire something more lubricious and moisturizing.

Tampon manufacturers want applicators made of inexpensive, low-cost materials that are easy, rapid and inexpensive to manufacture at high volumes and tampons that can be assembled at high speeds with only minor modifications. Current tampon offerings are deficient in one or more of these attributes.

While various lubricants have been mentioned in the prior art as a means of improving slip, the literature does not teach specific lubricants or resins to use, the necessary levels required to improve slip, the specific, quantified improvements, or the process and machinery modifications required to allow molded articles containing such lubricants to be assembled at high volumes and high speeds.

Accordingly, there remains a need in the art for a molded article, such as a tampon applicator, that is efficiently produced and has soft, flexible and lubricious properties desired by the consumer. The present disclosure meets this need by providing a lubricious polymeric composition and articles molded from the lubricious polymeric composition.

SUMMARY OF THE INVENTION

The present disclosure provides a lubricious polymeric composition that comprises polymer and one or more lubricants.

The present disclosure also provides such a composition that provides enhanced lubricity to an article formed from said composition.

The present disclosure further provides a tampon applicator formed from the lubricious polymeric composition.

The present disclosure still further provides such a tampon applicator having enhanced lubricity.

The present disclosure also provides a process for forming a tampon applicator with said lubricious polymeric composition.

To accomplish the foregoing benefits and advantages, the present disclosure provides a lubricious polymeric composition that includes a polymer and one or more lubricants.

Articles formed from the lubricious polymeric composition possess enhanced softness, flexibility and lubricity. In one embodiment, one or more components of a tampon applicator are molded from the lubricious composition.

The present disclosure also provides methods for making and assembling an article formed from a lubricious polymeric composition comprising polymer and one or more lubricants. In one embodiment, a process for forming one or more components of a tampon applicator is provided.

DETAILED DESCRIPTION OF THE INVENTION

The present disclosure provides a lubricious composition. Lubricious as defined herein means having a smooth and slippery quality. The lubricious composition is an enhanced polymeric compound or composition that includes a combination of polymer and one or more lubricants. Articles formed from this lubricious composition exhibit improved properties, such as, softness, flexibility and lubricity, to the user. While it is envisioned that this enhanced polymeric composition may be used to form a variety of products, such as, for example, baby or nurser bottles and holders, pacifiers, toothbrushes and containers, a preferred application is for catamenial devices. In one embodiment, the enhanced polymeric composition is used in forming one or more components of a tampon applicator.

The primary component of the enhanced polymeric composition is one or more polymers. Suitable polymers for use in the present disclosure include, but are not limited to, polyolefins, such as, polyethylene, low density polyethylene, high density polyethylene, near low density polyethylene, block copolymers comprised of polyethylene or polystyrene as one block and polyisoprene, polybutadiene or other elastomeric polymer as another block, polypropylene, PET (polyethylene terephthalate), nylon, polystyrene, polyvinyl chloride, polymethyl methacrylate; biodegradable or water-soluble polymers, such as thermoplastic, moldable starch, polyvinyl alcohol, aliphatic and/or aromatic polyesters; or any combinations thereof.

In one embodiment of the present disclosure, the polymer is a combination of low density polyethylene and high density polyethylene. In another embodiment of the present disclosure, the polymer is only low density polyethylene.

In one embodiment of the present disclosure, the polymer is about 50 percent by weight (wt. %) to about 99 wt. % of the total weight of the polymeric composition. In another embodiment, the polymer is about 80 wt. % to about 99 wt. % of the total weight of the polymeric composition. In another embodiment, the polymer is about 95 wt. % to about 99.5 wt. % of the total weight of the polymeric composition.

Another important component in the polymeric composition of the present disclosure is one or more lubricants present in an amount sufficient to adjust the lubricity of an article formed from the polymeric composition.

Suitable lubricant for use in the present disclosure includes, but is not limited to, fatty acid amide, erucamide, oleamide, stearamide, stearyl erucamide, bis-erucamide, metallic stearate, calcium stearate, ethylene bis stearamide, ethylene bis oleamide, glycerol monostearate, magnesium stearate, calcium stearate, zinc stearate, aluminum di-stearate, fatty acid glycerol esters, calcium soaps of montanic acids, triglycerol esters of hydroxy saturated fatty acids, ethylene methyl acrylate copolymer, Teflon (polytetrafluoroethylene), micronized PTFE, mineral oil, Teflon micropowder, C14-18 alkyl di(2-hydroxyethylamine), sodium alkane sulfonates such as Nucrel, dimethicone and other polydimethyl siloxanes (such as those sold by Dow-Corning as Medical Fluids 360, which are available at various viscosities, t-Butyldiphenylchlorosilane, other polar aromatic and aliphatic silanes such as chloromethyldimethylchlorosilane, epoxylated soybean oil, oxidized polyethylene wax, K-Y jelly, glycerol, or any combinations thereof.

It is possible to use other, comparable types of lubricants and/or resins, some in combination. Many are surfactant-like, that is, they are both hydrophobic and possess polar functionality. The polar functionality tends to allow this material to bloom to the surface.

In one embodiment according to the present disclosure, the one or more lubricants are erucamide, stearyl erucamide, bis-erucamide, or any combinations thereof. Erucamides have been found to be particularly beneficial since they can undergo substantial blooming subsequent to molding. Such blooming can result in a migration of the erucamide to the surface of the molded polymeric article that can result in a highly lubricious molded article. This has been found to be particularly advantageous to tampon applicator barrels and/or plungers formed from the polymeric composition of the present disclosure.

The one or more lubricants are present in the polymeric composition of the present disclosure in an amount about 0.001 wt. % to about 40 wt. %, based on the total weight of the polymeric composition. Preferably, the one or more lubricants are present in an amount about 0.01 wt. % to about 20 wt. %, based on the total weight of the polymeric composition. More preferably, the one or more lubricants are present in an amount about 0.1 wt. % to about 1 wt. %, based on the total weight of the polymeric composition. In one embodiment, where one or more erucamides are used, the one or more erucamides are present in an amount about 0.12 wt. % to about 0.55 wt. %, based on the total weight of the polymeric composition.

The polymeric composition may further include one or more additional components selected from the group consisting of thermoplastic elastomer, plasticizer, compatibilizer/flow modifier, pigment, pearlescent, antioxidant, antistatic agent, filler, reinforcements, dye, mineral, surfactant, light/UV stabilizer, thermal stabilizer, impact modifier, processing aid, extender, flame retardant, biocide, fungicide, antiozonant, blowing agent, foaming agent, or any combinations thereof.

There are a wide variety of additives, additive classes, resins and resin types that are known to those skilled in the art of plastics applications and plastics formulations. Usage levels in plastics vary greatly, depending upon the application requirements. Examples of additives can be found in texts such as *Additives for Plastics*, ed. J. Thuen and N. Mehlberg, published by D.A.T.A and the International Plastics Selector, Inc., San Diego, Calif., 1$^{st}$ edition, 1987. Examples of plastics are provided in the *D.A.T.A. Digest: Plastics, Thermoplastics and Thermosets*, Volumes 1 and 2, published by D.A.T.A and the International Plastics Selector, Inc., San Diego, Calif., 11$^{th}$ edition, 1990.

In one embodiment of the present disclosure, it is desirable to use one or more pigments and pearlescents. Suitable pigments and pearlescents for use in the present disclosure may include, but are not limited to, titanium dioxide, mica, colorant, carbon black, phthalate ester, quinacridone red, phthalo (GS) blue phthalate esters, lead chromate, inorganic aluminosilicate, cadmium sulfoselenide, cadmium sulfide, barium sulfate, or any combinations thereof. In one embodiment, a combination of titanium dioxide, mica and colorant is used.

When used, the pigment (and pearlescent) is present in an amount about 0.01 wt. % to about 5 wt. % based on the total weight of the polymeric composition. Preferably, the pigment is present in an amount about 0.2 wt. % to about 2 wt. % based on the total weight of the polymeric composition. More preferably embodiment, the pigment is present in an amount about 0.5 wt. % to about 1.2 wt. % based on the total weight of the polymeric composition.

It is to be understood that an antistatic agent or antistat may be added to the polymeric compound or composition. The antistat imparts a slight to moderate degree of electrical conductivity to plastic compounds, thus preventing the accumulation of electrostatic charges on the molded article. However, it has been found that because of the polar functionality associated with the one or more lubricants of the present disclosure, the need for antistat is diminished or all together removed.

While the polymeric composition may be compounded by any suitable method known in the art, in one embodiment of the present disclosure the polymeric composition is compounded as follows. All ingredients are weighed and then combined in a twin-screw extruder to form a melted compound. The melted compound is then extruded and cut into pellets, which are then injection molded to form the desired shape for the molded article.

To further demonstrate the novel aspects of the present disclosure, molded tampon applicators formed from the polymeric composition of the present disclosure are exemplified below. These examples are in no way intended to limit the scope of the present disclosure.

In one embodiment, where it is desirable to minimize costs, it is preferable that the tampon applicator have an applicator barrel that uses the polymeric compound of the present disclosure, while the plunger is made, perhaps, of less expensive material. A softer applicator barrel is more comfortable and is a desirable feature of a tampon applicator in order to provide improved ease of insertion. Accordingly, the examples are directed to a tampon applicator barrel, however it should be understood that any component of the tampon applicator, including the barrel and plunger, may be formed from the polymeric composition of the present disclosure.

In one embodiment according to the present disclosure, a tampon applicator barrel is formed from a polymeric composition comprising about 98 wt. % to about 99 wt. % LDPE, about 0.6 wt. % mica, about 0.5 wt. % titanium dioxide, about 0.25 wt. % erucamide, and less than about 0.01 wt. % colorant.

In another embodiment according to the present disclosure, a tampon applicator plunger is formed from a polymeric composition comprising about 92 wt. % to about 93 wt. % HDPE, about 5 wt. % LDPE, about 0.9 wt. % mica, about 0.75 wt. % titanium dioxide, about 0.37 wt. % erucamide, and less than about 0.01 wt. % colorant.

EXAMPLES

First, the different slip agents and resins had to be added to LDPE. Most of these ingredients have been approved by the FDA for food contact. Typically, these ingredients were compounded together with a mixture of pigments, minerals and some LDPE to produce special color/slip agent concentrates. Both this concentrate (a masterbatch) and additional LDPE were simultaneously added separately to an injection-molding machine. In some cases color concentrate was omitted, whereas in others, three feeds were added: lubricant, resin or masterbatch as one feed; color concentrate; and LDPE.

Compounding is typically done using an extruder, in which the ingredients, typically thermoplastics or else lower to medium molecular weight polar lubricants, are mixed, melted at high temperatures and then conveyed by a screw to a die, at which point pellets were produced using a pelletizer. Some additives, for example, dimethicones, are liquids, and may require special extruders capable of handling liquid feeds.

Table 1 below lists some of the ingredients that were used in the examples and, by way of example, the companies that supply or manufacture them.

TABLE 1

Ingredients Used in the Examples

| Ingredient | Abbreviation (used in examples) | Trade Name/ Grade | Manufacturer | Comment |
|---|---|---|---|---|
| Erucamide | ER | Crodamide E | Croda | (also available from others, e.g. Crompton and Akzo Nobel) |
| Low Density Polyethylene (no erucamide) | LDPE | Marlex KN226 | Chevron-Phillips | (also available from others, e.g. ExxonMobil) |
| Low Density Polyethylene (with erucamide) | LDPE-ER | Marlex KN226B | Chevron-Phillips | (also available from others, e.g. ExxonMobil) |
| Ethylene bis stearamide | EBS | Advawax 280 | Rohm and Haas | |
| Glycerol Monostearate | GMS | Advalube F1005 | Rohm and Haas | |
| Ethylene Methyl Acrylate Copolymer | E-MA | Elvaloy 1224 EAC ST | DuPont | |
| Teflon Micropowder | TM | Teflon PFA Grade 350 | " | |
| LDPE-C14-C18 alkyl di(2-hydroxyethyl) amine | CE | Cesa_Stat-TPI-3103 | DuPont/ Clariant | |
| Humidifying Polymer | HP | DPO AD1059 | DuPont (developmental product) | Anti-stat |
| Nucrel-Sodium Alkane sulfonate) Masterbatch | HO | HostaStat-WR 990139 | DuPont/ Clariant | |
| Dimethicone, 350 centistokes | DM-350 | Medical Fluid 360, 350 cst. | Dow-Corning | |
| Dimethicone, 1000 centistokes | DM-1000 | Medical Fluid 360, 1000 cst. | " | |
| 72% K-Y Jelly/ 28% Glycerol Mix | K-Y/G | K-Y Jelly and Glycerol | McNeil PPC (J&J) | Glycerol available from many sources. |

Table 2 provides the compositions of the tampon barrels that were made to exemplify this disclosure. Most examples used the Gentle Glide standard Super (absorbency) barrel mold tool. Example #9 used the smaller, Regular (absorbency) size barrel mold, while Examples #10 through #17 and Comparative Example #2 were run using a new mold tool.

TABLE 2

Additional Ingredients for the Various Examples (Amounts of LDPE and Lubricant(s) are provided in rightmost column)

| Example # | Additional Ingredients | CAS Number for these | Amounts Used in Barrel | LDPE and Lubricants |
|---|---|---|---|---|
| #1 | Mica | 12001-26-2 | 0.6785% | 98.85% LDPE, 0.135% ER |
| | Titanium Dioxide | 13463-67-7 | 0.2025% | |
| | Zinc Stearate | 557-05-1 | 0.1245% | |
| | Colorants: Ultramarine blue & Pigment Red 122 | 57455-37-5 and 980-26-7 | <0.01% (total of both) | |
| Comparative Example #1 | Mica | 12001-26-2 | 0.6785% | 98.99% LDPE, no lubricant |
| | Titanium Dioxide | 13463-67-7 | 0.2025% | |
| | Zinc Stearate | 557-05-1 | 0.1245% | |
| | Colorants: Ultramarine blue & Pigment Red 122 | 57455-37-5 and 980-26-7 | <0.01% (total of both) | |

TABLE 2-continued

Additional Ingredients for the Various Examples (Amounts of LDPE and Lubricant(s) are provided in rightmost column)

| Example # | Additional Ingredients | CAS Number for these | Amounts Used in Barrel | LDPE and Lubricants |
|---|---|---|---|---|
| #2 | Mica | 12001-26-2 | 0.6785% | 98.71% |
| | Titanium Dioxide | 13463-67-7 | 0.2025% | LDPE, |
| | Zinc Stearate | 557-05-1 | 0.1245% | 0.270% ER |
| | Colorants: | 57455-37-5 | <0.01% | |
| | Ultramarine blue & | and | (total of | |
| | Pigment Red 122 | 980-26-7 | both) | |
| #3 | Mica | 12001-26-2 | 0.848% | 98.46% |
| | Titanium Dioxide | 13463-67-7 | 0.253% | LDPE, |
| | Zinc Stearate | 557-05-1 | 0.156% | 0.270% ER |
| | Colorant: | 57455-37-5 | <0.01% | |
| | Ultramarine blue | | | |
| #4 | Mica | 12001-26-2 | 0.6785% | 98.44% |
| | Titanium Dioxide | 13463-67-7 | 0.2025% | LDPE, |
| | Zinc Stearate | 557-05-1 | 0.1245% | 0.540% ER |
| | Colorants: | 57455-37-5 | <0.01% | |
| | Ultramarine blue & | and | (total of | |
| | Pigment Red 122 | 980-26-7 | both) | |
| #5 (same as #2) | Mica | 12001-26-2 | 0.6785% | 98.71% |
| | Titanium Dioxide | 13463-67-7 | 0.2025% | LDPE, |
| | Zinc Stearate | 557-05-1 | 0.1245% | 0.270% ER |
| | Colorants: | 57455-37-5 | <0.01% | |
| | Ultramarine blue & | and | (total of | |
| | Pigment Red 122 | 980-26-7 | both) | |
| #6 | Mica | 12001-26-2 | 0.6785% | 98.98% |
| | Titanium Dioxide | 13463-67-7 | 0.2025% | LDPE, |
| | Zinc Stearate | 557-05-1 | 0.1245% | 0.005% (50 ppm) |
| | Colorants: | 57455-37-5 | <0.01% | ER |
| | Ultramarine blue & | and | (total of | |
| | Pigment Red 122 | 980-26-7 | both) | |
| #7 | Mica | 12001-26-2 | 0.6785% | 98.26% |
| | Titanium Dioxide | 13463-67-7 | 0.2025% | LDPE, 0.27% |
| | Zinc Stearate | 557-05-1 | 0.1245% | ER, 0.45% |
| | Colorants: | 57455-37-5 | <0.01% | EBS |
| | Ultramarine blue & | and | (total of | |
| | Pigment Red 122 | 980-26-7 | both) | |
| #8 | Mica | 12001-26-2 | 0.6785% | 98.26% |
| | Titanium Dioxide | 13463-67-7 | 0.2025% | LDPE, 0.27% |
| | Zinc Stearate | 557-05-1 | 0.1245% | ER, |
| | Colorants: | 57455-37-5 | <0.01% | 0.45% GMS |
| | Ultramarine blue & | and | (total of | |
| | Pigment Red 122 | 980-26-7 | both) | |
| #9 | Mica | 12001-26-2 | 0.6785% | 98.71% |
| | Titanium Dioxide | 13463-67-7 | 0.2025% | LDPE, 0.27% |
| | Zinc Stearate | 557-05-1 | 0.1245% | ER |
| | Colorants: | 57455-37-5 | <0.01% | |
| | Ultramarine blue & | and | (total of | |
| | Pigment Red 122 | 980-26-7 | both) | |
| #10 | Mica | 12001-26-2 | 0.808% | 84.51% |
| | Titanium Dioxide | 13463-67-7 | 0.241% | LDPE, 14.3% |
| | Zinc Stearate | 557-05-1 | 0.148% | E-MA |
| | Colorant: | 57455-37-5 | <0.01% | |
| | Ultramarine blue | | | |
| #11 | Mica | 12001-26-2 | 0.808% | 79.75% |
| | Titanium Dioxide | 13463-67-7 | 0.241% | LDPE, 19.0% |
| | Zinc Stearate | 557-05-1 | 0.148% | TM |
| | Colorant: | 57455-37-5 | <0.01% | |
| | Ultramarine blue | | | |
| #12 | Mica | 12001-26-2 | 0.808% | 89.27% |
| | Titanium Dioxide | 13463-67-7 | 0.241% | LDPE, 9.5% |
| | Zinc Stearate | 557-05-1 | 0.148% | CE |
| | Colorant: | 57455-37-5 | <0.01% | |
| | Ultramarine blue | | | |
| #13 | Mica | 12001-26-2 | 0.808% | 65.46% |
| | Titanium Dioxide | 13463-67-7 | 0.241% | LDPE, 33.3% |
| | Zinc Stearate | 557-05-1 | 0.148% | HP |
| | Colorant: | 57455-37-5 | <0.01% | |
| | Ultramarine blue | | | |
| #14 | Mica | 12001-26-2 | 0.808% | 89.27% |
| | Titanium Dioxide | 13463-67-7 | 0.241% | LDPE, 9.5% |
| | Zinc Stearate | 557-05-1 | 0.148% | HO |
| | Colorant: | 57455-37-5 | <0.01% | |
| | Ultramarine blue | | | |

TABLE 2-continued

Additional Ingredients for the Various Examples (Amounts of LDPE and Lubricant(s) are provided in rightmost column)

| Example # | Additional Ingredients | CAS Number for these | Amounts Used in Barrel | LDPE and Lubricants |
|---|---|---|---|---|
| #15 | Mica | 12001-26-2 | 0.808% | 89.27% |
|  | Titanium Dioxide | 13463-67-7 | 0.241% | LDPE, 9.5% |
|  | Zinc Stearate | 557-05-1 | 0.148% | DM-350 |
|  | Colorant: Ultramarine blue | 57455-37-5 | <0.01% |  |
| #16 | Mica | 12001-26-2 | 0.808% | 89.27% |
|  | Titanium Dioxide | 13463-67-7 | 0.241% | LDPE, 9.5% |
|  | Zinc Stearate | 557-05-1 | 0.148% | DM-1000 |
|  | Colorant: Ultramarine blue | 57455-37-5 | <0.01% |  |
| Comparative Example #2 | Mica | 12001-26-2 | 0.808% | 98.73% |
|  | Titanium Dioxide | 13463-67-7 | 0.241% | LDPE, no |
|  | Zinc Stearate | 557-05-1 | 0.148% | lubricant |
|  | Colorant: Ultramarine blue | 57455-37-5 | <0.01% |  |
| #17 | Mica | 12001-26-2 | 0.808% | 95.94% |
|  | Titanium Dioxide | 13463-67-7 | 0.241% | LDPE, 2.86% |
|  | Zinc Stearate | 557-05-1 | 0.148% | of a mix of |
|  | Colorant: Ultramarine blue | 57455-37-5 | <0.01% | 82% KY-Jelly and 18% glycerol |

A large, commercial Nestal HP 3500 injection-molding machine was used to produce many of the injection molded barrel parts (those in Examples #1 through #8 and Comparative Example #1 in Table 2). This multi-cavity mold was used to make the tampon applicator barrels rapidly and efficiently. A smaller single-cavity injection-molding machine was used to make the barrels in Examples #9 through #17 and Comparative Example #2.

Most of the compounded pellets made were of good quality. The tampon applicator barrels produced were of very good quality. Many of the applicators were inspected and virtually no observable scratching or scuffing marks were found.

Tampon applicator barrels were then tested using various tests, mainly those relating to lubricity. The HP 400 machines used are described in U.S. Pat. No. 4,321,993, by Alfred Hinzmann and Erich Presser (Hauni-Richmond, Inc.), Mar. 30, 1982. This patent (henceforth designated '993) describes the HP 400 machines in some detail. The disclosure of the '993 patent is hereby incorporated by reference herein in its entirety.

In the first trials, only tampons from Example #6 and Comparative Example #2 could be properly assembled. The problem was that barrels made with ingredients used in the other examples were so slippery that they fell off these machines at some point. Sometimes the barrels fell off at the lifting movement interrupting elements (location 47 of FIG. 4 of the '993 patent), sometimes at the barrel storage hopper (location 26 of FIG. 2 of the '993 patent), sometimes at the conveyor (location 23 of the '993 patent) used to the assembling station (location 25 of the '993 patent), sometimes at or right after the heating drum (location 31 of the '993 patent) or the cooling drum (location 32 of the '993 patent). Loss of tampons was so great that this process was untenable. Transfers between drums or disks or hoppers relied on some level of barrel friction.

Therefore, a second trial was done on two modified HP400 tampon machines (Playtex Hauni). In preparation for this trial, the same compounds (color concentrate masterbatches) were used, but new sets of barrels were injection molded. Different injection molding machines were used, but similar examples were generated. Again, no problems with injection molding were observed. Examples of barrels and tampons made in this subsequent trial are designated with an "R" suffix in the following Tables.

In the second trial, all tampons assembled, even those of Example #4R, which contains a high lubricant level, could be assembled with the new set of slippery barrels without any problems. It was unexpectedly found that one key machine modification resulted in the successful trial. The modification to the transfers between the various hoppers, drums and discs (see the '993 patent) was accomplished by using vacuum. Typically, it was found that about 60+ inches of water (a little more than about 2.2 pounds per square inch (absolute) of negative pressure) should be supplied to the machine and distributed using headers to various locations in the machine, e.g. transfer drums, in order to manufacture/assemble tampons with slippery barrels effectively. Use of suction, rather than friction, allows the slippery barrels to remain on these drums, instead of slipping off the carriers and holders due to the combination of gravitational and centrifugal forces.

Additional modifications included: 1) using a bowl feeder (Service Engineering, Inc., Greenfield, Ind.) to feed and orient the barrels properly rather than lifting up the slippery barrels; 2) carriers used to convey the tampons from drum carousel to drum carousel were realigned and were replaced using softer, less abrasive materials; 3) installation of a small guard belt to keep the barrels from slipping out of the hopper improperly; and 4) a tiny guard was put in place to keep the plunger or pusher inside the barrel, once these applicator parts were combined in the HP 400.

With these machine and process modifications in place, surprisingly, even the slipperiest barrels could be assembled to form high-quality tampons cleanly, easily, economically and efficiently, at the high speeds required for these high volume, FDA-regulated class II medical devices.

Test Descriptions and Results

Various testing was done to show the advantages of these new lubricious tampon applicators. Generally, the test results are presented for both the first and second trials.

Ejection Force

Tampon ejection force is measured in the laboratory by a special test. The assembled tampon is gripped using two fingers on either side of the fingergrip. The force in ounces exerted on a high precision weighing scale (a Weightronix WI-130 load cell) to eject the pledget is measured. The data is recorded electronically on a spreadsheet. Playtex® Gentle Glide® control tampon samples were also tested. Table 3 provides some key results for the ejection force testing.

TABLE 3

Ejection Force Testing of Tampons

| Example (Barrel Identification) | Average Ejection Force (oz.) | Std. Dev and Number of Repeats | Comment |
|---|---|---|---|
| Results, First Trial | | | |
| Comparative #1 | 28.5 | 7.7 (10) | No ER, Super |
| Gentle Glide Control | 32.1 | 3.8 (10) | No ER, Super |
| #5 | 18.0 | 7.7 (10) | 0.27% ER, fast molding cycle time, Super |
| #7 | 15.4 | 4.4 (10) | ER + EBS, Super |
| #4 | 20.0 | 11.3 (10) | 0.54% ER, Super |
| Results, Second Trial | | | |
| #1R | 21.6 | 1.8 (33) | 0.135% ER, Super |
| Comparative #1R | 33.5 | 3.9 (33) | No ER, Super |
| #6R | 35.1 | 3.9 (33) | 50 ppm ER, resin blend, Super |
| #2R | 21.0 | 1.1 (33) | 0.27% ER, repeat, Super |
| #5R | 20.8 | 2.2 (33) | 0.27% ER, fast molding cycle time, repeat, Super |
| #4R | 20.4 | 1.9 (33) | 0.54% ER, repeat, Super |
| #9R | 16.8 | 1.8 (33) | 0.27% ER, repeat, Regular |

As the data indicates, while there is some variability, there are big differences in ejection force in comparing tampons whose barrels contain 0.135% or more erucamide vs. those that have little (50 ppm) or no erucamide. At levels according to the present disclosure, the ejection force is less than about 21 oz. Also, it appears that once the lubricant reaches a certain critical value, the ejection force levels off.

Environmental Stability

Environmental stability of tampons is very important. Often, consumers store their tampons in hot, humid environments. Because pledgets are made of cellulosic fibers, at high temperatures and high humidity, such pledgets can increase in moisture content, causing some pressure to be exerted against the sides of the barrel and making ejection difficult.

To test for environmental stability, several tampon applicator barrels were placed into an environmental chamber, unwrapped, for one week. Then, the barrels were removed and re-tested for ejection force. Table 4 provides the testing results.

TABLE 4

Environmental Stability of Tampons (Ejection Force Re-tested after subjecting tampons to 90 deg F., 90% Relative Humidity, one week, unwrapped)

| Example (Barrel Identification) | Average Ejection Force (oz.) | Std. Dev and Number of Repeats | Comment |
|---|---|---|---|
| #1R | 75.6 | 11.6 (27) | 0.135% ER, Super |
| Gentle Glide Control | 92.4 | 13.5 (16) | No ER, Super |
| Comparative #1R | 109.1 | 5.8 (11) | No ER, Super |
| #6R | 100.3 | 9.1 (15) | 50 ppm ER, resin blend, Super |
| #2R | 73.4 | 12.3 (14) | 0.27% ER, repeat, Super |
| #5R | 68.8 | 8.8 (15) | 0.27% ER, fast molding cycle time, repeat, Super |
| #4R | 72.2 | 13.4 (14) | 0.54% ER, repeat, Super |
| #9R | 30.0 | 4.6 (14) | 0.27% ER, repeat, Regular |

As with the initial ejection force values, as presented in Table 3, Table 4 shows that the environmental stability of tampons with at least 0.135% erucamide is much better than that of the comparable controls or than that for tampons whose erucamide levels are 50 ppm or lower.

Coefficient Of Friction

Tampon applicator barrel samples were tested for coefficient of friction (CoF). The CoF was measured using a slight variant of ASTM D1894 (tensile type) coefficient of friction test, adapting for tampons, since this test is often used for films. Two different Instron 4411 (Instron, Canton, Mass.) machines were used, one for the initial trial and the other for the second trial. The Series IX Windows software provided with the modern Instron machines allows the test methods to be programmed in and instructions retained on a database.

The slight modifications we used to test coefficient of friction for tampons and barrels are as follows:
1) A thin-gauge nylon wire was attached on one side to a hook suspended from the top of the Instron (which has a 500 N load cell) and on the other to a hook which was attached to a small, stainless steel, 3"×4" sled that had been covered with felt and supported by a long (6" wide by 18" long stainless steel platen. The wire was pulled through a small wheel (pulley) at the edge of that platen and redirected vertically at a 90° angle to the top of the Instron.
2) Either four barrels or four fully assembled tampons (i.e. with pledget, plunger and barrel, and strings cut, to keep these from exerting drag on the stainless steel platen) were tested. These were attached to the underside of the sled, with the barrel's petals facing toward the Instron 4411 machine and positioned to be even with the front of the sled.
3) The sled, including tampons, was weighed on a top-loading analytical balance to the nearest +/−0.1 grams.
4) The sled was positioned on the stainless steel platen, with the back of the tampons nearly flush with the backmost edge of the platen and with the wire taut.
5) The Instron was tared and calibrated, to ensure that the weights and positions for the different runs were compared on an equal basis.
6) The Instron pulled the sled at a constant velocity towards its load cell, using constant tension on the wire. It was pulled at a rate of 6 inches per minute for a total displacement of 5 inches. The data acquisition system tracked the load vs. distance at 200 to 500 x-y points.
7) The static coefficient of friction is defined as the maximum load needed to move the sled the first 0.1 inches divided by the combined weight of the sled plus tampons. Since two different Instron machines were used with very slightly different calibration procedures, this static coefficient of friction was normalized by measuring this first for the comparative example sample (either Results for the normalized coefficients of friction, as measured by the test method above, are provided in Table 5. Non-normalized coefficients were in the 0.2 to 0.3 range, similar to that observed for sheets of low-density polyethylene, as reported by "Engineering Properties of Marlex™ Resins", a CD entitled "Technical Literature for Molding & Durables Customers" available from Chevron-Phillips Chemical Company, Bartlesville, Okla.

TABLE 5

Coefficient of Friction (CoF) Results

| Example (Barrel Identification) | Type of CoF (static or kinetic) and item (barrel or full tampons) | Average Normalized CoF | Std. Dev. (CoF) | Number of Repeats | Comment |
|---|---|---|---|---|---|
| Initial Trial | | | | | |
| Comparative | Static | 1.00 | 0.18 | 4 | No ER, |
| Comparative | Static | 1.00 | 0.09 | 8 | No ER, |
| Comparative | Kinetic | 1.00 | 0.12 | 4 | No ER, |
| Comparative | Kinetic | 1.00 | 0.08 | 8 | No ER, |
| #2 | Static | 0.80 | 0.09 | 4 | 0.27% ER, |
| #2 | Static | 0.82 | 0.14 | 4 | 0.27% ER, |
| #2 | Kinetic | 0.86 | 0.07 | 4 | 0.27% ER, |
| #2 | Kinetic | 0.84 | 0.11 | 4 | 0.27% ER, |
| #5 | Static | 0.82 | 0.05 | 4 | 0.27% ER, fast molding time, |
| #5 | Kinetic | 0.83 | 0.03 | 4 | 0.27% ER, fast molding time, |
| #4 | Static | 0.81 | 0.07 | 4 | 0.54% ER, |
| #4 | Kinetic | 0.80 | 0.05 | 4 | 0.54% ER, |
| #7 | Static | 0.93 | 0.05 | 4 | ER and EBS, |
| #7 | Kinetic | 0.92 | 0.05 | 4 | ER and EBS, |
| #8 | Static | 0.95 | 0.06 | 4 | ER and GMS, |
| #8 | Static | 0.87 | 0.09 | 4 | ER and GMS, |
| #8 | Kinetic | 0.91 | 0.09 | 4 | ER and GMS, |
| #8 | Kinetic | 0.89 | 0.10 | 4 | ER and GMS, |
| Second Trial | | | | | |
| Comparative | Static | 1.00 | 0.05 | 4 | No ER, Super, |
| Comparative | Kinetic | 1.00 | 0.23 | 4 | No ER, Super, |
| #6R | Static | 1.03 | NA | 1 | 50 ppm ER, Resin Super, |
| #6R | Kinetic | 0.88 | NA | 1 | 50 ppm ER, Resin Super, |
| #1R | Static | 0.84 | 0.00 | 2 | 0.135% ER, Super, |
| #1R | Kinetic | 0.82 | 0.08 | 2 | 0.135% ER, Super, |
| #4R | Static | 1.03 | NA | 1 | 0.54% ER, Super, |
| #4R | Kinetic | 0.75 | NA | 1 | 0.54% ER, Super, |
| #5R | Static | 0.84 | 0.00 | 2 | 0.27% ER, fast molding time, repeat, |
| #5R | Kinetic | 0.82 | 0.08 | 2 | 0.27% ER, fast molding time, repeat, |
| #9R | Static | 0.96 | 0.00 | 2 | 0.27% ER, Regular, |
| #9R | Kinetic | 0.80 | 0.08 | 2 | 0.27% ER, Regular, |

1 or #1R), then all other static coefficient of friction values were divided by this value. This placed all coefficients on an equivalent basis.
8) The kinetic coefficient of friction is defined as the average load needed to move the sled with tampons from the 0.1 inch point to the 5 inch point, dividing by the combined weight of the sled plus tampons. It, too, was normalized, using a procedure identical to that above for the static coefficients of friction.
9) Usually, the procedure was repeated at least two or three times, mainly because of the variability associated with the test.
10) Calculations and statistical comparisons were made by downloading the data from the Instron 4411 to a Microsoft Excel spreadsheet to conduct the analysis.

As Table 5 shows, even though there is some variability in the non-normalized coefficients, addition of the various lubricants according to the present disclosure lowers the coefficient of friction, as opposed to the comparative examples, whether the testing is done for barrels or for tampons and whether the measurement is static CoF or kinetic CoF. Particularly, tampon components formed with a composition according to the present disclosure exhibit an average normalized CoF that is about 5% to about 20%, and more particularly about 10% to about 20%, less than an average normalized CoF for comparative examples without lubricant.

Syngyna Absorbency

Syngyna absorbency is a very important feature of tampons. Syngyna absorbency is used by the US government, specifically the FDA, in order to regulate tampons and to help ensure their safety for use by consumers. Syngyna absorbency is a standard test (see the FDA *Federal Register*, 21 CFR Ch. 1 (Apr. 1, 1995 edition), paragraph 801.430, "User Labeling for Menstrual Tampons"). Super absorbency tampons are regulated by this test to be within the range of 9 to 12 grams of absorbed fluid, while Regular absorbency tampons must be within the range of 6 to 9 grams of fluid absorbed. 90% of the tampons must be within this range 90% of the time.

Table 6 provides the Syngyna absorbency results for tampons made by this disclosure.

TABLE 6

Syngyna Absorbency of Tampons

| Example (Barrel Identification) | Average Syngyna Absorbency (grams) | Std. Dev and Number of Repeats | Comment |
|---|---|---|---|
| #1R | 10.88 | 0.42 (33) | 0.135% ER, Super |
| Comparative #1R | 10.87 | 0.67 (33) | No ER, Super |
| #6R | 10.58 | 0.44 (33) | 50 ppm ER, resin blend, Super |
| #2R | 10.77 | 0.43 (33) | 0.27% ER, repeat, Super |
| #5R | 10.86 | 0.52 (33) | 0.27% ER, fast molding cycle time, repeat, Super |
| #4R | 10.80 | 0.39 (33) | 0.54% ER, repeat, Super |
| #9R | 7.72 | 0.38 (33) | 0.27% ER, repeat, Regular |

As is evident from the data, there is no effect of the lubricant on Syngyna absorbency. Also, both the Regular and Super tampons are well within the specified ranges, as regulated by the US government.

Profileometry, Tampon Barrels

Surface smoothness was assessed using a Pocket Surf II Profilometer (Mahr Federal, available from Penn Tool, N.J.). This hand-held instrument has a diamond stylus to contact a solid object. By running the stylus across the object's surface, it provides a digital readout of the root-mean-square variation of the mean surface roughness in microns.

Table 7 provides data on the surface roughness of barrels, as measured in accordance with the above-described instrument. The average results for surface smoothness are slightly lower for the first trial vs. that for the second trial. This difference is likely due to the surface smoothness of the cavities on the different injection molding machines used. There appears to be no statistical evidence of an effect of the lubricant on surface smoothness of the barrels by this test.

TABLE 7

Surface Smoothness of Barrels

| Example (Barrel Identification) | Mean Roughness (microns) | Std. Dev and Number of Repeats | Comment |
|---|---|---|---|
| First Trial | | | |
| Comparative #1 | 0.706 | 0.096 (32) | No ER, Super |
| #5 | 0.750 | 0.107 (32) | 0.27% ER, fast cycle time, Super |
| #4 | 0.769 | 0.104 (32) | 0.54% ER, Super |
| Second Trial | | | |
| Gentle Glide Control | 0.856 | 0.129 (12) | Super |
| Gentle Glide Control | 0.912 | 0.113 (12) | Regular |
| #4R | 0.865 | 0.068 (12) | 0.54% ER, Super, Repeat |
| #9R | 0.886 | 0.091 (12) | 0.27% ER, repeat, Regular |
| #6R | 0.879 | 0.145 (12) | 50 ppm ER, resin blend, Super |

While the instant disclosure has been described with reference to one or more exemplary embodiments, it will be understood by those skilled in the art that various changes may be made and equivalents may be substituted for elements thereof without departing from the scope thereof. In addition, many modifications may be made to adapt a particular situation or material to the teachings of the disclosure without departing from the scope thereof. Therefore, it is intended that the disclosure not be limited to the particular embodiment(s) disclosed as the best mode contemplated for carrying out this disclosure.

We claim:

1. A tampon applicator comprising a barrel, a plunger or both a barrel and plunger formed from a lubricious polymeric composition consisting essentially of:
   about 95 wt % to about 99.5 wt %, based on the weight of the polymeric composition, of low density polyethylene, high density polyethylene, or a combination thereof; and
   one or more lubricants selected from the group consisting of erucamide, stearyl erucamide, bis-erucamide, and any combinations thereof.

2. The tampon applicator of claim 1, wherein the tampon applicator comprises said barrel, and wherein said barrel has an average ejection force less than about 21 ounces.

3. The tampon applicator of claim 1, wherein the tampon applicator comprises said barrel, and wherein said barrel has a normalized coefficient of friction about 5% to about 20% less than a normalized coefficient of friction of a barrel formed from a composition without one or more lubricants.

4. The tampon applicator of claim 1, wherein said one or more lubricants are present in an amount about 0.1 wt % to about 1 wt %, based on the total weight of the polymeric composition.

5. The tampon applicator of claim 1, wherein said composition further comprises about 0.5 wt % to about 1.2 wt %, based on the total weight of the polymeric composition, of one or more pigments and pearlescents selected from the group consisting of titanium dioxide, mica, colorant, carbon black, phthalate esters, quinacridone red, phthalo (GS) blue phthalate esters, lead chromate, inorganic aluminosilicate, cadmium sulfoselenide, cadmium sulfide, barium sulfate, and any combinations thereof.

* * * * *